US012680112B2

(12) United States Patent
Zheng et al.

(10) Patent No.: US 12,680,112 B2
(45) Date of Patent: Jul. 14, 2026

(54) GENE TRANSFECTION SYSTEM AND METHOD

(71) Applicant: SHENZHEN INSTITUTES OF ADVANCED TECHNOLOGY, Shenzhen (CN)

(72) Inventors: Hairong Zheng, Shenzhen (CN); Long Meng, Shenzhen (CN); Congzhi Wang, Shenzhen (CN); Xiufang Liu, Shenzhen (CN); Yuchen Wang, Shenzhen (CN); Wei Zhou, Shenzhen (CN); Lili Niu, Shenzhen (CN); Xiaowei Huang, Shenzhen (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 1376 days.

(21) Appl. No.: 17/297,067

(22) PCT Filed: Jul. 26, 2018

(86) PCT No.: PCT/CN2018/097151
§ 371 (c)(1),
(2) Date: May 26, 2021

(87) PCT Pub. No.: WO2020/019224
PCT Pub. Date: Jan. 30, 2020

(65) Prior Publication Data
US 2022/0033853 A1     Feb. 3, 2022

(51) Int. Cl.
*C12N 15/87* (2006.01)
*B01L 3/00* (2006.01)
*C12M 1/42* (2006.01)

(52) U.S. Cl.
CPC .......... *C12N 15/87* (2013.01); *B01L 3/50273* (2013.01); *B01L 2300/123* (2013.01);
(Continued)

(58) Field of Classification Search
None
See application file for complete search history.

(56) References Cited

U.S. PATENT DOCUMENTS

2006/0281172 A1* 12/2006 Kuwabara .............. C12M 25/00
435/305.2
2018/0045681 A1* 2/2018 Mohapatra ......... G01N 29/2462
(Continued)

FOREIGN PATENT DOCUMENTS

CN      103981090 A      8/2014
CN      105535968 A      5/2016
(Continued)

OTHER PUBLICATIONS

Precision Micro-Optics Inc., https://www.pmoptics.com/LiNbO3.
html (pdf) (Year: 2016).*

(Continued)

*Primary Examiner* — James Lin
*Assistant Examiner* — Brittany I Fisher
(74) *Attorney, Agent, or Firm* — Westman, Champlin & Koehler, P.A.

(57) ABSTRACT

The gene transfection system includes an acoustothermal module and a signal generating module; the acoustothermal module includes a piezoelectric substrate, an acoustothermal chip arranged on the piezoelectric substrate and N sound-absorbing vessels arranged on the acoustothermal chip and used for cultivating recipient cells, and N is an integer greater than or equal to 1; the signal generating module is used to output basic frequency signals; the acoustothermal chip is used to convert the basic frequency signal to an acoustic wave signal, establish a temperature gradient field with the acoustic wave signal, and control the temperature of the recipient cell in the sound-absorbing vessels with the temperature gradient field, so that the pores are opened on (Continued)

the membranes of the recipient cell, and the nucleic acids or other substances can go into the cells through these pores.

6 Claims, 6 Drawing Sheets

(52) U.S. Cl.
CPC .................. *B01L 2400/0436* (2013.01); *B01L 2400/0439* (2013.01)

(56) References Cited

U.S. PATENT DOCUMENTS

2018/0073029  A1      3/2018   Hardee et al.
2018/0334697  A1 *  11/2018   Shachar .................. A61L 29/16
2019/0031999  A1 *   1/2019   Suresh ................... C12M 23/16

FOREIGN PATENT DOCUMENTS

CN          108239661  A      7/2018
KR          101839574  B1     3/2018
WO      WO-2017127686  A1 *   7/2017   ............ C12M 23/16

OTHER PUBLICATIONS

Extended European Search Report from European Patent Application No. 18928020.9 dated Sep. 1, 2021.

International Search Report and Written Opinion of PCT/CN2018/097151, mailed Apr. 28, 2019; 7 pages.

Zhang, Anliang et al. "Heating Droplets in Parallel Using Surface Acoustic Wave" Chinese Journal of Sensors and Actuators, vol. 27, No. (9) Sep. 30, 2014, ISSN: 1004-1699, pp. 1221-1225.

Ramesan, S. et al. "Acoustically-mediated Intracellular Delivery." Nanoscale, vol. 10, Jul. 2, 2018, ISSN: 2040-3372, pp. 13165-13178.

Meng, L. et al. "On-Chip Targeted Single Cell Sonoporation with Microbubble Destruction Excited by Surface Acoustic Waves" Applied Physics Letter, vol. 104, Feb. 18, 2014, ISSN: 0003-6951, pp. 073701-1-5.

Greco, G. et al., "Surface Acoustic Wave (SAW)-Enhanced Chemical Functionalization of Gold Films." Sensors, vol. 17, Oct. 26, 2017, ISSN: 1424-8220, pp. 1-11.

* cited by examiner

GENE TRANSFECTION SYSTEM AND METHOD

CROSS-REFERENCE TO RELATED APPLICATION

This Application is a Section 371 National Stage Application of International Application No. PCT/CN2018/097151, filed Jul. 26, 2018 and published as WO 2020/019224 A1 on Jan. 30, 2020, not in English. The contents of all of the aforementioned applications, including any intervening amendments thereto, are incorporated herein by reference.

TECHNICAL FIELD

The application relates to the field of cell biology, in particular to a gene transfection system and method.

BACKGROUND

Gene therapy is a high-tech biomedical technology that introduces human normal genes or genes with therapeutic effect into human target cells in a certain way to correct gene defects or exert therapeutic effects, so as to achieve the purpose of treating diseases. It can be seen that it is important for how to accurately and efficiently insert foreign genes into the appropriate recipient cells of the patient by gene transfection technologies. At present, the most commonly used non-viral gene transfection methods are electroporation, cationic liposome Lipofectamine™ 2000, sonicporation and photoporation, of which electroporation and cationic liposome Lipofectamine™ 2000 are the most commonly used ones.

However, the ability of cells for accepting exogenous nucleic acids varies greatly with their different growth characteristics and in-vitro culture conditions. In addition, the existing non-viral transfection methods have disadvantages such as being difficult to be excreted from the body, high energy, high toxicity, low efficiency on certain types of cells such as primary immune cells, and requiring expensive special equipment, which greatly limit their application in the practical gene therapy.

Technical Problem

The main purpose of the present invention is to propose a novel gene transfection system and method to solve the existing problems in the current non-viral transfection methods, such as being difficult to be excreted from the body, high toxicity, low efficiency on certain types of cells, etc., which greatly limit their application in the practical gene therapy.

Technical Solution

In order to achieve the above purpose, the first aspect of the present invention provides a gene transfection system, which includes an acoustothermal module and a signal generating module;

the acoustothermal module includes a piezoelectric substrate, an acoustothermal chip arranged on the piezoelectric substrate, and N sound-absorbing vessels arranged on the acoustothermal chip. The vessels are used for culturing recipient cells. N is an integer greater than or equal to 1;

the signal generating module is used to output a basic frequency signal;

the acoustothermal chip is used to convert the basic frequency signal to generate an acoustic wave signal, and with the acoustic wave signal, a temperature gradient field is established in the sound absorbing vessels, and with the temperature gradient field, the temperature of the recipient cells in the sound-absorbing vessels can be precisely controlled, so that the pores are opened on the membranes of the recipient cells, and the nucleic acids or other substances can go into the cells through these pores.

With reference to the first aspect of the present invention, in a first embodiment of the first aspect of the present invention, the acoustothermal chip includes M interdigital transducers, a first drive unit, and a second drive unit, where M is an integer greater than or equal to 1;

the sound-absorbing vessel is arranged on the interdigital transducer;

the interdigital transducer is used to generate an acoustic wave signal based on the basic frequency signal;

the first drive unit is used to individually control the finger period in each of the interdigital transducers;

the second drive unit is used to periodically activate part or all of the interdigital transducers;

the first drive unit and the second drive unit are also used to construct an array of the interdigital transducers to change the thermal field distribution in the acoustothermal chip.

In a first embodiment of the first aspect of the present invention, the interdigital transducer further changes the thermal field distribution in the acoustothermal chip based on the shape of its electrode.

In a first embodiment of the first aspect of the present invention, the second drive unit simultaneously activates a group of interdigital transducers in the same one-dimensional direction;

the first drive unit controls the finger period of a group of interdigital transducers in a one-dimensional direction to change in a gradient;

the first drive unit and the second drive unit construct a two-dimensional interdigital transducer array.

In a first embodiment of the first aspect of the present invention, the interdigital transducer is arranged on the piezoelectric substrate, and the sound-absorbing vessel is arranged on the interdigital transducer.

In combination with the first aspect of the present invention, in a second embodiment of the first aspect of the present invention, the sound-absorbing vessels are partially or all made of polydimethylsiloxane (PDMS), and each vessel contains an independent chamber.

In a second embodiment of the first aspect of the present invention, the bottom of the chamber is further coated with polylysine.

In combination with the first aspect of the present invention, in a third embodiment of the first aspect of the present invention, the piezoelectric substrate is a 128° Y-cut X-propagation, double-side polished lithium niobate (LiNbO3) substrate.

The second aspect of the present invention provides a gene transfection method, which is applied to a gene transfection system which includes an acoustothermal module and a signal generating module;

the acoustothermal module includes a piezoelectric substrate, an acoustothermal chip arranged on the piezoelectric substrate, and N sound-absorbing vessels arranged on the acoustothermal chip. The vessels are used for culturing recipient cells, N is an integer greater than or equal to 1;

the gene transfection method includes:

outputting a basic frequency signal by the signal generating module;

converting the basic frequency signal by the acoustothermal chip to an acoustic wave signal, and establishing a temperature gradient field in the sound-absorbing vessel with the acoustic wave signal; precisely controlling the temperature of the culture medium in the sound-absorbing vessel with the temperature gradient field, so that the pores are opened on the membranes of the recipient cells, and the nucleic acids or other substances can go into the cells through these pores.

With reference to the second aspect of the present invention, in a first embodiment of the second aspect of the present invention, the acoustothermal chip includes M interdigital transducers, where M is an integer greater than or equal to 1;

the sound-absorbing vessel is arranged on the interdigital transducer;

converting the basic frequency signal to an acoustic wave signal, and establishing a temperature gradient field in the sound-absorbing vessel with the acoustic wave signal includes:

activating part or all of the interdigital transducers periodically in the acoustothermal chip, individually controlling the finger period in each of the interdigital transducers, constructing an array of interdigital transducers and changing the thermal field distribution in the acoustothermal chip.

In a first embodiment of the second aspect of the present invention, changing the thermal field distribution in the acoustothermal chip further includes:

changing the thermal field distribution in the acoustothermal chip by changing the electrode shape of the interdigital transducer.

In a first embodiment of the second aspect of the present invention, the gene transfection method further includes:

simultaneously activating a group of interdigital transducers in the same one-dimensional direction;

controlling the finger period of the group of interdigital transducers in the same one-dimensional direction to change in a gradient;

constructing a two-dimensional interdigital transducer array by the gradient change of the finger period.

With reference to the second aspect of the present invention, in a second embodiment of the second aspect of the present invention, the sound-absorbing vessels are partially or all made of polydimethylsiloxane (PDMS), and each vessel contains an independent chamber.

In a second embodiment of the second aspect of the present invention, the bottom of the chamber is further coated with polylysine.

In combination with the second aspect of the present invention, in a third embodiment of the second aspect of the present invention, the piezoelectric substrate is a 128° Y-cut X-propagation, double-side polished lithium niobate (LiNbO3) substrate.

Beneficial Effects

In the gene transfection system and method proposed in the present invention, the basic frequency signal in the signal generating module is converted into an acoustic wave signal by the acoustothermal chip of the acoustothermal module, and the temperature of the sound-absorbing vessel is precisely controlled with the acoustic wave signal, so that the pores are opened on the membranes of the recipient cells in the sound-absorbing vessel, thereby changing the permeability of the membrane of the recipient cells, increasing the success rate of the nucleic acids or other substances entering the recipient cells, and improving the transfection efficiency of genes; the instrument used in the present invention is simple, which means the cost can be very low. All these advantages make the present invention to be a potential substitute technology in the practical gene therapy field.

DETAILED DESCRIPTION OF THE DRAWINGS

The realization of the purposes, functional characteristics and advantages of the present invention will be further described in conjunction with the embodiments and with reference to the accompanying drawings.

DETAILED DESCRIPTION OF THE EMBODIMENTS

It should be understood that the specific embodiments described here are only used to explain the present invention, but not to limit the present invention.

It should be noted that in this application, the terms "include", "comprise" or any other variants thereof are intended to cover non-exclusive inclusion, so that a process, method, article or device including a series of elements not only includes those elements, but also other elements that are not explicitly listed, or elements inherent to the process, method, article, or device. If there are no more restrictions, the element defined by the sentence "including a . . . " does not exclude the existence of other same elements in the process, method, article, or device that includes the element.

In this application, the use of suffixes such as "module", "part" or "unit" used to denote elements is only for facilitating the description of the present invention, and has no specific meaning itself. Therefore, "modules" and "parts" can be used interchangeably.

In the following description, the serial numbers of the embodiments of the application are for description only, and do not represent the advantages and disadvantages of the embodiments.

Embodiment 1

Figure 1:
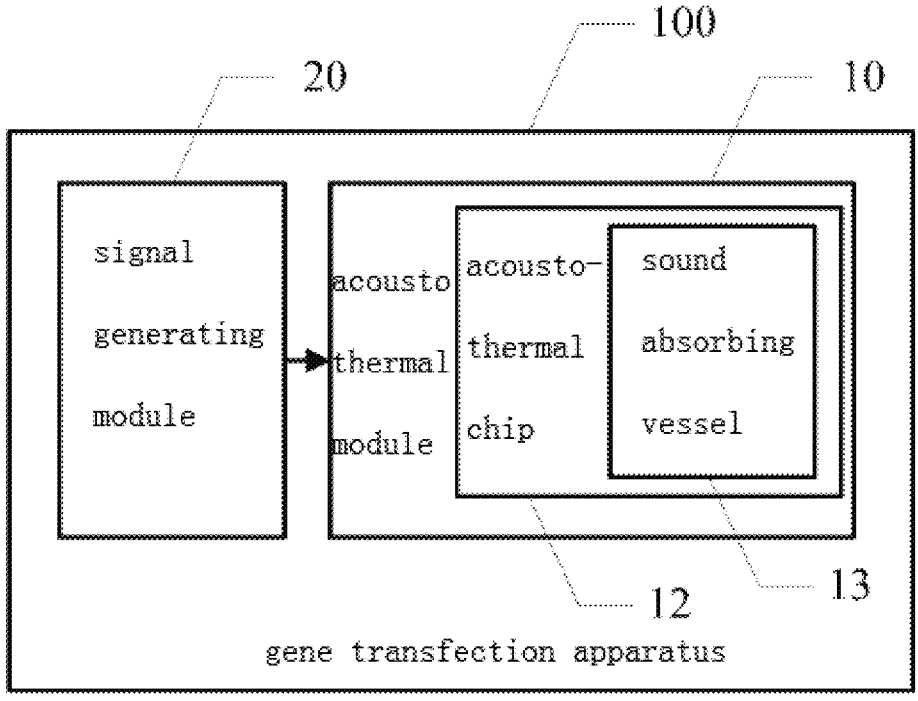
FIG. 1 is a schematic structural diagram of a gene transfection system provided in embodiment 1 of the present invention.

As shown in FIG. 1, an embodiment of the present invention provides a gene transfection system 100, which includes an acoustothermal module 10 and a signal generating module 20;

the acoustothermal module 10 includes a piezoelectric substrate 11, an acoustothermal chip 12 arranged on the piezoelectric substrate 11 (not shown in the drawings), and N sound-absorbing vessels 13 arranged on the acoustothermal chip 12, where N is an integer greater than or equal to 1.

In the embodiment of the present invention, the piezoelectric substrate 11 (not shown in the drawings) is used to provide a passageway for the propagation of the acoustic waves and the electric current in the acoustothermal chip.

In an embodiment, the piezoelectric substrate 11 may be a 128° Y-cut X-propagation, double-side polished lithium niobate (LiNbO3) substrate.

In the embodiment of the present invention, the sound-absorbing vessel 13 is used for culturing the recipient cells.

In a specific application, the sound-absorbing vessel can be made of some kinds of sound-absorbing material to absorb the energy from the acoustic wave and convert it into heat energy which can increase the temperature in the chamber by increasing the temperature of its wall; before using the sound-absorbing vessel to culture the recipient cells, the recipient cells have been cultured in other containers for a period of time, processed, and then placed in the sound-absorbing vessel.

The so-called sound-absorbing material can be rubber, viscous liquid, perforated plywood, perforated metal plate and wood wool sound-absorbing board; the thickness of the sound-absorbing material in the sound-absorbing vessel is not limited in the embodiment of the present invention, that is, there may be no space left as the thickness of the chamber, or there also may be a certain space left as the thickness of the chamber. The shape and size of the sound-absorbing vessel are not limited to a small cylinder or cube. If an open and circular vessel is used, it is easier for cell culture and the transfer of heat energy; and if a sealed rectangular vessel is used, it will ensure the sterile cultivation of the cells.

In practical applications, the sound-absorbing vessel limits the working range of the acoustothermal effect. When the acoustic wave is reflected and refracted multiple times by the PDMS film, its energy is absorbed by the PDMS film and converted into thermal energy. This process can be accurately controlled to localize the working range of acoustothermal effect, and the accuracy can reach micron level.

In one embodiment, the gene transfection system provided by the embodiment of the present invention can be also used to realize the function of polymerase chain reaction (PCR) by precisely controlling the temperature of different regions; in a specific application, it can also be used for the manipulation of organisms and polystyrene microspheres and droplets, and the realization of PCR by gas sensors and cell lysis, etc.

In one embodiment, the sound-absorbing vessels are made of polydimethylsiloxane (PDMS), and each PDMS vessel contains an independent chamber.

In practical applications, PDMS can absorb more acoustic energy than liquid samples and other materials (such as glass or silicon). It can quickly increase the temperature of the liquid samples (about 2000 K/s) with an adequate input power.

In one embodiment, the bottom of the chamber of the PDMS vessel is also coated with polylysine. If the PDMS vessel is filled with liquid samples of suspension cells, they can easily adhere and grow on the surface of its bottom.

In the embodiment of the present invention, the signal generating module 20 is used to output a basic frequency signal.

In a specific application, the signal generating module can be any circuit and electronic components that can output electrical frequency signals, such as signal generators and crystal oscillators.

In the embodiment of the present invention, the acoustothermal chip 12 is used to convert the basic frequency signal to an acoustic wave signal, and establish a temperature gradient field in the sound-absorbing vessel, and precisely control the temperature of the culture medium in the sound-absorbing vessel, so that the pores are opened on the membranes of the recipient cells, and the nucleic acids or other substances can go into the cells through these pores.

In a specific application, the acoustothermal chip can be any pattern, shape and size. It can convert the basic frequency signal to an acoustic wave signal, absorb the acoustic wave signal, convert the acoustic energy in the acoustic wave signal into thermal energy, and precisely control the temperature of a specific location on the acoustothermal chip. It can be a chip composed of an interdigital transducer, a PDMS vessel and a piezoelectric substrate.

In a specific application, the temperature gradient field is a set of temperature values (in degrees Celsius) with gradient changes established based on the changes of the acoustic wave signal. Each temperature value corresponds to an acoustic wave signal strength (in dB), and also corresponds to the perforation effect on the membranes of recipient cells in a PDMS vessel. For example, when the intensity of the acoustic wave signal is A dB, the temperature in the sound-absorbing vessel controlled by the acoustothermal chip is B ° C. At this time, the membranes of recipient cells in the liquid samples can be perforated to a certain level which is named as 100%; then when the temperature in the sound-absorbing vessel needs to be controlled to B ° C., thus the intensity of the acoustic wave signal needs to be controlled at A dB based on the temperature gradient field, so that the perforation effect on the membranes of recipient cells can reach the level of 100%.

Those skilled in the art can understand that, in the gene transfection system provided by the embodiment of the present invention, it also includes passageways for the propagation of acoustic wave and electric current signals, which can be arranged on the piezoelectric substrate, such as metal bridges, conductive metal holes, silicon wafers and so on.

In the embodiment of the present invention, the working principle of the gene transfection system 100 is as follows:

when the acoustothermal chip convert the basic frequency signal to an acoustic wave signal, the acoustic wave signal propagates along the substrate and enters the PDMS vessel, it will reflect and refract at the interfaces between the PDMS vessel and the substrate, and between the PDMS vessel and the liquid sample in it. For the 128° Y-cut X-propagation, lithium niobate (LiNbO3) piezoelectric substrate, the refractive angle of the Rayleigh wave is $\theta = \sin^{-1}(cp/cs) \approx 16°$, where cp is the speed of sound in the PDMS material. As the acoustic wave is absorbed by the PDMS material, the acoustic energy is converted into heat energy, increasing the temperature of the PDMS material in the PDMS vessel, so that the acoustothermal chip establishes a temperature gradient field in the PDMS vessel, then the recipient cells in the PDMS vessel are affected by the heat energy in this temperature gradient field, and the perforation effect occurs on the membranes of the recipient cells at a specific temperature.

In the gene transfection system provided by the embodiment of the present invention, in one respect, the basic frequency signal in the signal generating module is converted into an acoustic wave signal by the acoustothermal chip of the acoustothermal module, and the temperature of the sound-absorbing vessel containing the recipient cells is precisely controlled, so that the perforation effect occurs on the membrane of the recipient cells, thereby changing their permeability, increasing the success rate of the nucleic acids or other substances entering into the cells, and improving the transfection efficiency of gene; in another respect, the PDMS material is used in the embodiment of the present invention to prepare the sound-absorbing vessel, which expands the control range of temperature, and increases the efficiency of the perforation effect on the membranes of the recipient cells; and the structure of the instrument used in the embodiment of the present invention is simple, which will reduce the cost and improves the practicability of the gene therapy compared with the traditional gene transfection methods.

EMBODIMENTS OF THE PRESENT INVENTION

Embodiment 2

Figure 2:
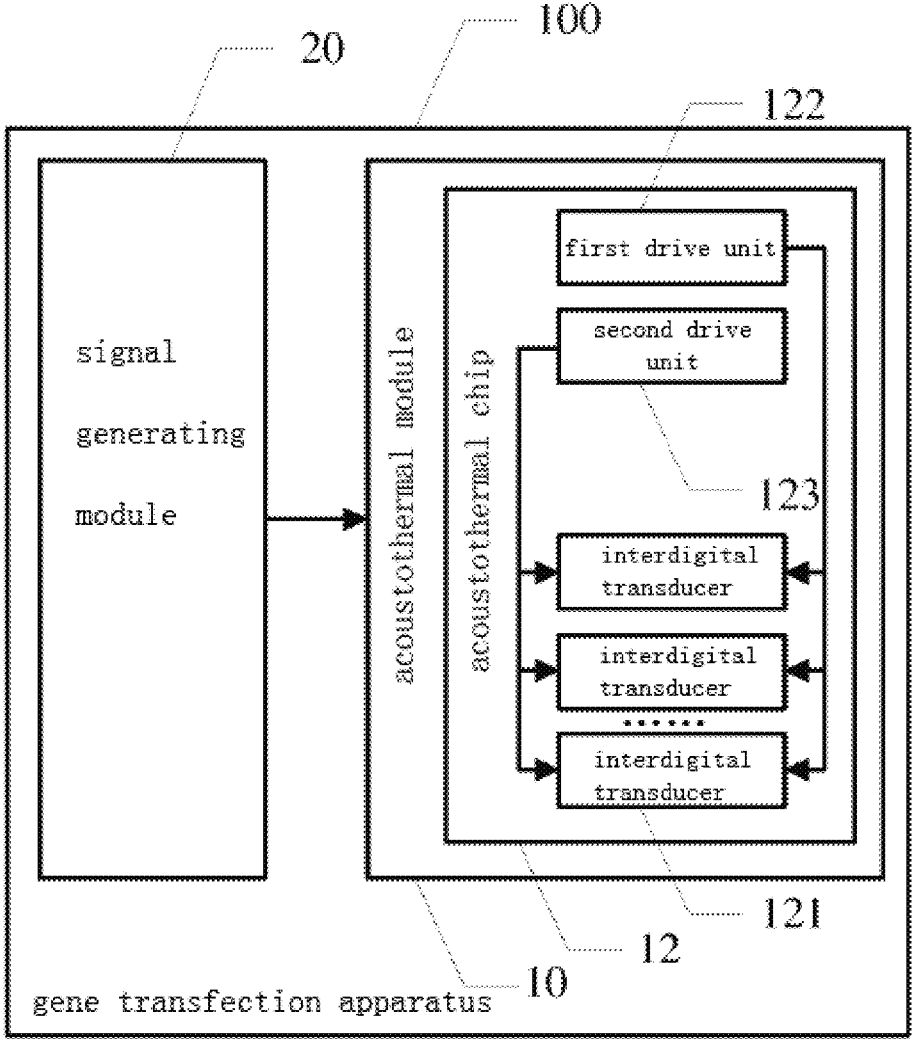
FIG. 2 is a schematic structural diagram of a gene transfection system provided in embodiment 2 of the present invention.

As shown in FIG. 2, the acoustothermal chip 12 in embodiment 1 includes M interdigital transducers 121, a first drive unit 122, and a second drive unit 123, where M is an integer greater than or equal to 1, and the sound-absorbing vessel 12 (not shown in the drawings) may be arranged on the interdigital transducer 121.

In one embodiment, there are N sound-absorbing vessels, and N is an integer greater than or equal to 1.

In the embodiment of the present invention, there is no number correspondence between the interdigital transducer and the sound-absorbing vessel, that is, one interdigital transducer does not necessarily correspond to one sound-absorbing vessel, and two interdigital transducers also do not necessarily correspond to one or two sound-absorbing vessels. When there are a plurality of interdigital transducers and one sound-absorbing vessel, the sound-absorbing vessel is arranged in one of the interdigital transducers, and the experiment is carried out with this interdigital transducer. For example, when there are four interdigital transducers and one sound-absorbing vessel in the gene transfection system, the gradient field is selected according to the temperature, then the frequency that can reach this temperature is determined, and the interdigital transducer which can create this frequency can be selected from the four interdigital transducers, then the sound-absorbing vessel should be arranged on the interdigital transducer for the following experiment; when there are a plurality of sound-absorbing vessels and a plurality of interdigital transducers, the interdigital transducer can correspond to the sound-absorbing vessel, thereby forming a plurality of interdigital transducers which are allocated to the sound-absorbing vessels, so as to realize a high-throughput and large-scale gene transfection.

In the embodiment of the present invention, the interdigital transducer 121 is used to convert the basic frequency signal to an acoustic wave signal. In a specific application, the intensity of the acoustic wave signal generated by the interdigital transducer is related to the metal film material of the interdigital transducer, the finger period, the size of the acoustic aperture and the other parameters.

In the embodiment of the present invention, the first drive unit 122 is used to individually control the finger period in each interdigital transducer. In a specific application, a number of interdigital transducers with different finger periods are used as separated heat sources to construct an independently controllable two-dimensional array, and the activation of each interdigital transducer can be recorded by a thermal imager. That is, the flexible and controllable heating of specific areas is realized by preparing an array of different types of interdigital transducers.

In the embodiment of the present invention, the second drive unit 123 is used to periodically activate part or all of the interdigital transducers. In a specific application, the second drive unit activates a plurality of interdigital transducers at the same time by the time-sharing control of the signal generator.

In the embodiment of the present invention, the first drive unit 122 and the second drive unit 123 are also used to construct an array of the interdigital transducers to change the thermal field distribution in the acoustothermal chip.

In one embodiment, the second drive unit simultaneously activates a group of interdigital transducers in the same one-dimensional direction; the first drive unit controls the finger period of a group of interdigital transducers in a one-dimensional direction to change in a gradient; the first drive unit and the second drive unit construct a two-dimensional interdigital transducer array.

In a specific application, the finger period of the interdigital transducer corresponds to the AC/DC driving frequency in the signal generating module. By changing the signal frequency that matches the finger period, a single interdigital transducer can be independently controlled; a plurality of interdigital transducers can be activated at the same time by the time-sharing control of the signal generating module. Therefore, when the finger period of the interdigital transducers changes gradually in each one-dimensional direction, an independently controllable two-dimensional interdigital transducer array can be constructed.

In an embodiment, the interdigital transducer also changes the thermal field distribution in a acoustothermal chip based on the shape of its electrodes. In a specific application, the spatial controllability of the temperature field can be changed by changing the shape and the arrangement of the interdigital electrodes; for example, when the shape of the electrodes is round or arc, the thermal field distribution will also be corresponding to round or arc shape.

The gene transfection system provided by the embodiment of the present invention realizes the temperature controllability in both time and space by preparing an array of different types of interdigital transducers, so that the heating area is flexible and controllable. Therefore, the advantages of high throughput, large-scale, rapid perforation of cell membranes, high safety and stability and no need to introduce synthetic microbubbles of this gene transfection system are realized, so that the low-cost and high-efficiency gene transfection can be realized.

Embodiment 3

The embodiments of the present invention aim at the gene transfection system provided in embodiment 1 and 2 above, and the experimental data are used to exemplify the beneficial effects in its practical application.

In the embodiment of the present invention, a cell model for gene transfection is established, and a comparison of the proposed method and the cationic liposome method (using Lipofectamine™ 2000) is conducted on gene transfection efficiency. In this embodiment, the effects of the gene transfection system described in the above embodiment 1 and embodiment 2 is demonstrated in practical application. The specific process of establishing a comparative experiment of gene transfection effect is as follows:

1. selecting the tumor cells of human breast cancer (MCF-7), the normal endothelial cells of human umbilical vein (HUVEC) and the normal microvascular endothelial cells of mouse brain (Bend.3) as the cell models.

2. treating the PDMS vessel, using polylysine to coat the bottom of the PDMS vessel, so that the cells can easily grow on the surface of its bottom.

3. using the green fluorescent protein (GFP) DNA as the target molecule to transfect the above three kinds of cells, and observing the green fluorescence under a fluorescent microscope to compare the gene transfection effect of the proposed gene transfection system and the cationic liposome method (using Lipofectamine™ 2000).

Figures 3, 4:
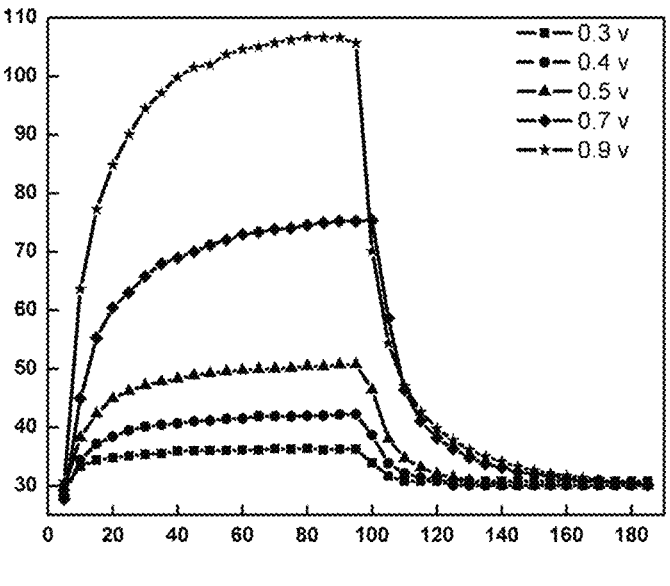
FIG. 3 is an experimental data diagram of the gene transfection system provided in embodiment 3 of the present invention.
FIG. 4 is an experimental data diagram of another gene transfection system provided in embodiment 3 of the present invention.

FIG. 3 and FIG. 4 is when the input basic frequency signal is stopped, the temperature change with time of the PDMS vessel on the top of the interdigital transducer, under the same frequency and different acoustic intensity (corresponding to sound pressure), in the comparative experiment of the gene transfection effect provided by the embodiment of the present invention. In FIG. 3, the x-axis represents time in seconds (s); the y-axis represents temperature in degrees Celsius (° C.); the different types of lines represent different sound pressures in volts (V); in FIG. 4, the scale on the right represents the temperature change, where, at t=2.92 seconds, the temperature of the culture medium which containing the recipient cells is about 50° C.

In the embodiment of the present invention, by establishing a two-dimensional array of interdigital transducers, and using the time-sharing control of the signal generator, each interdigital transducer is used as a heat source to form a specific pattern.

In such a practical application, using LIpofectamine-2000 to transfect GFP-DNA to MCF-7, the transfection efficiency is high, reaching 98.34%.

Figure 5:
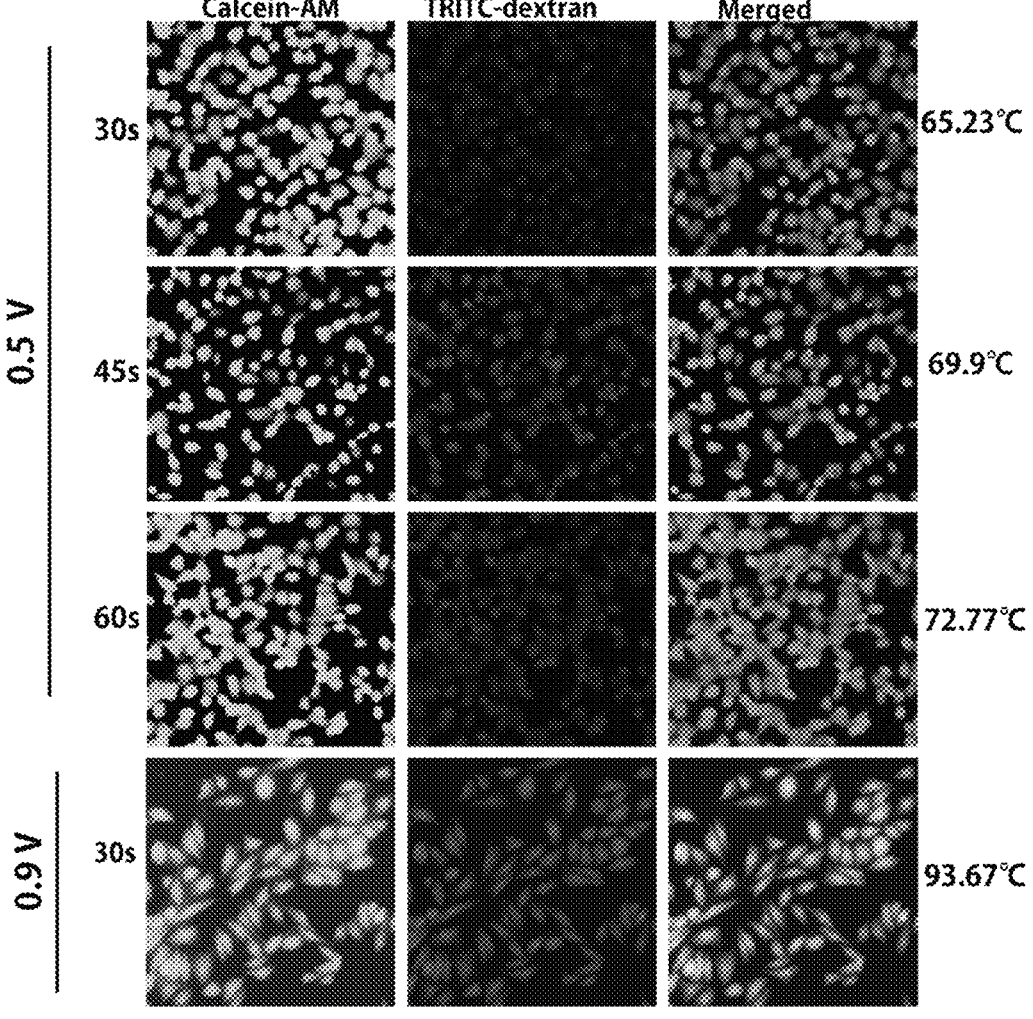
FIG. 5 is a schematic diagram of the experimental effects of the gene transfection system provided in embodiment 3 of the present invention.

FIG. 5 shows the gene transfection effect of using Lipofectamine™2000 to transfect GFP-DNA to MCF-7 cells, by the double staining method of tetramethylrhodamine isothiocyanate-labeled dextran (TRITC-Dextran) and calcein (Calcein-AM) and observing with fluorescence microscope, together with the results of using the proposed gene transfection system described in embodiment 1 and embodiment 2 above. The gene transfection process takes place in the proposed gene transfection system shown in FIG. 3 and FIG. 4. The results are shown in FIG. 5, that when the sound pressure is 0.5 V, the time is 30 s, 45 s, and 60 s, and the sound pressure is 0.9 V, the time is 30 s, the human breast cancer cells (MCF-7) occur reversible perforation with a high efficiency. It means, the cells still have high biological activity after the membrane perforation. In the gene transfection system described in the above-mentioned embodiment 1 and embodiment 2, the cells occurreversible perforation at the same level.

Embodiment 4

Figure 6:
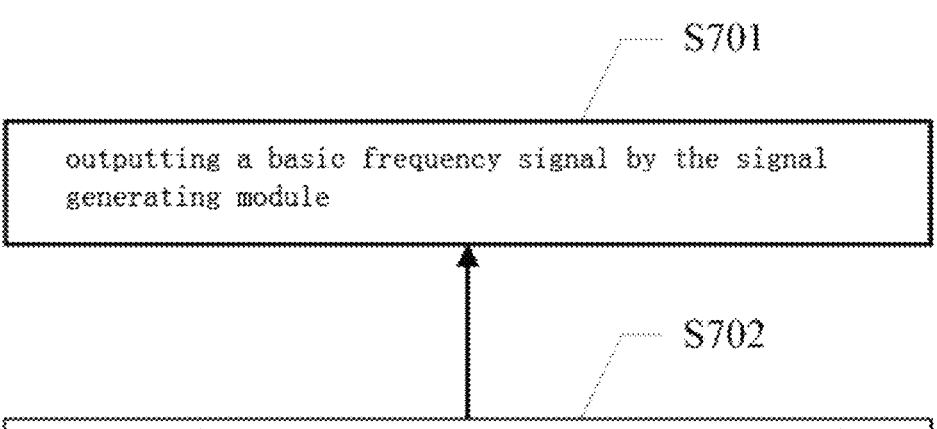
FIG. 6 is a schematic diagram of the process of the gene transfection method provided in embodiment 4 of the present invention.

As shown in FIG. 6, an embodiment of the present invention provides a gene transfection method, which is applied to a gene transfection system, and the gene transfection system includes an acoustothermal module and a signal generating module;

the acoustothermal module includes a piezoelectric substrate, an acoustothermal chip arranged on the piezoelectric substrate, and N sound-absorbing vessels arranged on the acoustothermal chip. The acoustic absorbing vessels are used for culturing recipient cells, and N is an integer greater than or equal to 1.

The steps of the gene transfection method include:

S701. outputting a basic frequency signal by the signal generating module;

S702. converting the basic frequency signal by the acoustothermal chip to an acoustic wave signal, and establishing a temperature gradient field in the sound-absorbing vessels; precisely controlling the temperature of the culture medium in the sound-absorbing vessel with the temperature gradient field, so that the recipient cell occurs membrane perforation.

In one embodiment, the piezoelectric substrate may be a 128° Y-cut X-propagation, double-side polished lithium niobate (LiNbO3) substrate.

In one embodiment, the sound-absorbing vessels are partially or totally made of polydimethylsiloxane (PDMS), and each PDMS vessel contains an independent chamber.

In practical applications, PDMS can absorb more acoustic energy than the liquid samples and other microchannel materials (such as glass or silicon), and can quickly increase the temperature of the liquid samples (about 2000 K/s).

In a specific application, the bottom of the PDMS vessel is coated with polylysine. If the PDMS vessel is filled with liquid samples containing suspension cells, the cells are easy to adhere and grow on the surface of its bottom.

In one embodiment, the acoustothermal chip includes M interdigital transducers, and M is an integer greater than or equal to 1; the sound-absorbing vessel is arranged on the interdigital transducer, the above step S702 includes:

By periodically activating part or all of the interdigital transducers in the acoustothermal chip, and individually controlling the finger period of each interdigital transducer, constructing an array of the interdigital transducers and changing the thermal field distribution in the acoustothermal chip.

Figure 7:
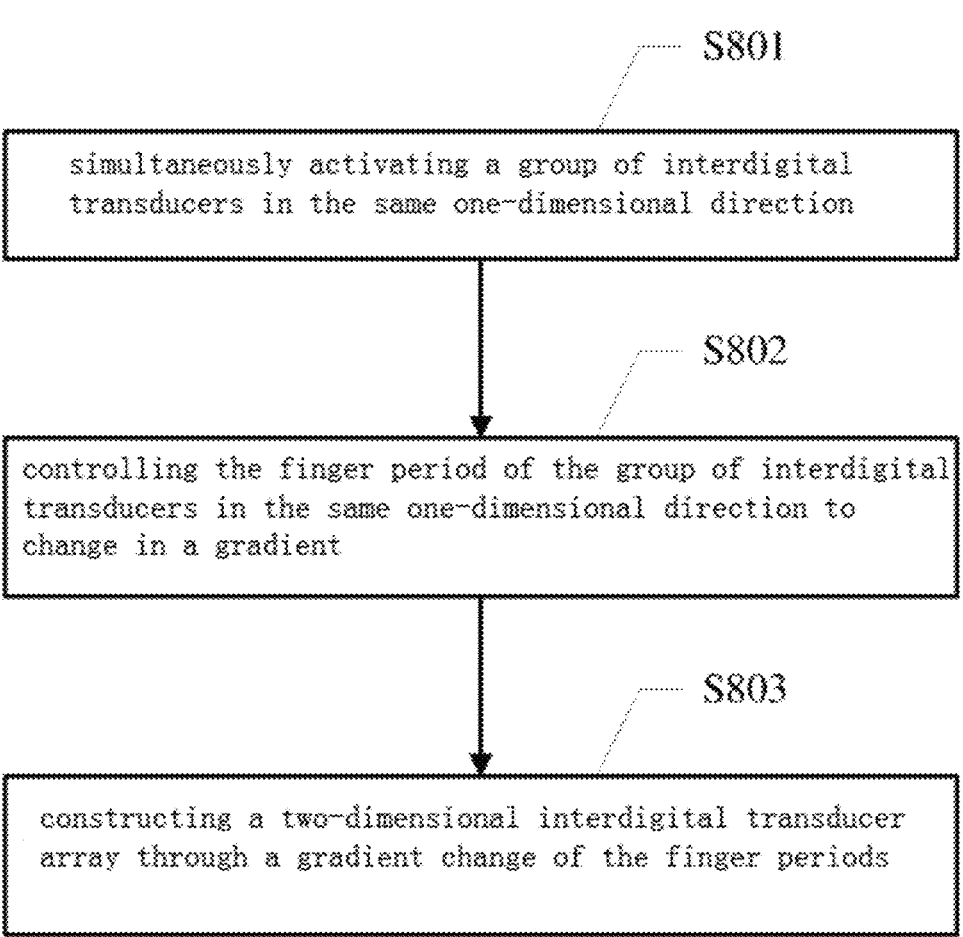
FIG. 7 is a schematic diagram of the process of another gene transfection method provided in embodiment 4 of the present invention.

As shown in FIG. 7, the embodiment of the present invention also provides an implementation that by periodically activating part or all of the interdigital transducers in the acoustothermal chip, and individually controlling the finger period of each interdigital transducer, constructing an array of the interdigital transducers and changing the thermal field distribution in the acoustothermal chip, including:

S801. simultaneously activating a group of interdigital transducers in the same one-dimensional direction.

S802. controlling the finger period of the group of interdigital transducers in the same one-dimensional direction to change in a gradient.

S803. constructing a two-dimensional interdigital transducer array through a gradient change of the finger periods.

In a specific application, the finger period of the interdigital transducer corresponds to the AC/DC driving frequency in the signal generating module. By changing the signal frequency that matches the cycle of the finger, independent control of a single interdigital transducer can be realized; at the same time, a plurality of interdigital transducers can be activated at the same time by the time-sharing control of the signal generating module. Therefore, when the finger period of the interdigital transducers changes gradiently in each one-dimensional direction, an independently controllable two-dimensional interdigital transducer array can be constructed.

In an embodiment, the changing thermal field distribution in the acoustothermal chip further includes changing thermal field distribution in the acoustothermal chip by changing the electrode shape of the interdigital transducer.

In the gene transfection method provided by the embodiment of the present invention, in one respect, the basic frequency signal in the signal generating module is converted into an acoustic wave signal by the acoustothermal chip of the acoustothermal module, and the temperature in the sound-absorbing vessel is precisely, so that the perforation effect occurs on the membrane of the recipient cells, thereby changing their permeability, increasing the success rate of the nucleic acids or other substances entering the cell, and improving the efficiency of gene transfection; in another respect, in the embodiment of the present invention, the PDMS material is used to prepare the sound-absorbing vessel, which increases the control range of temperature, and improves the success rate of the perforation effect on the membranes of the recipient cells; and the structure of the instrument used in the embodiment of the present invention is simple, which will reduce the cost and improves the practicability of the gene therapy compared with the traditional gene transfection methods.

The above are only preferred embodiments of the present invention and do not limit the scope of the present invention. Any equivalent structure or equivalent process transformation made by using the content of the description and drawings of the present invention, or directly or indirectly applied to other related technical fields, is also included in the scope of patent protection of the present invention.

INDUSTRIAL APPLICABILITY

In the gene transfection method provided by the embodiment of the present invention, in one respect, the basic frequency signal in the signal generating module is converted into an acoustic wave signal by the acoustothermal chip of the acoustothermal module, and the temperature in the sound-absorbing vessel is precisely, so that the perforation effect occurs on the membrane of the recipient cells, thereby changing their permeability, increasing the success rate of the nucleic acids or other substances entering the cell, and improving the efficiency of gene transfection; in another respect, in the embodiment of the present invention, the PDMS material is used to prepare the sound-absorbing vessel, which increases the control range of temperature, and improves the success rate of the perforation effect on the membranes of the recipient cells; and the structure of the instrument used in the embodiment of the present invention is simple, which will reduce the cost and improves the practicability of the gene therapy compared with the traditional gene transfection methods.

What is claimed is:

1. A gene transfection system, wherein the system comprises: an acoustothermal module and a signal generating module;

the acoustothermal module comprises: a piezoelectric substrate, an acoustothermal chip arranged on the piezoelectric substrate, and N sound-absorbing vessels arranged on the acoustothermal chip and configured for culturing recipient cells, wherein N is an integer greater than 1;

the signal generating module is configured to output a basic frequency signal;

the acoustothermal chip is configured to convert the basic frequency signal to an acoustic wave signal, establish a temperature gradient field in the sound-absorbing vessels with the acoustic wave signal, and precisely control the temperature of the recipient cells in the sound-absorbing vessels to a specified temperature that enables a perforation effect on membranes of the recipient cells to reach a level of 100% by controlling an intensity of the acoustic wave signal at a predetermined acoustic wave signal intensity based on the temperature gradient field, so that pores are opened on the membranes of the recipient cells, and nucleic acids or other substances are allowed to go into the recipient cells through these pores;

wherein the temperature gradient field is a set of temperature values with gradient changes established based on changes of the acoustic wave signal, each temperature value corresponds to an acoustic wave signal strength and also corresponds to a perforation effect on the membranes of the recipient cells in a sound-absorbing vessel;

wherein the acoustothermal chip comprises M interdigital transducers, a first controller, and a second controller; and M is an integer greater than 1;

the sound-absorbing vessels are made of polydimethylsiloxane (PDMS), and each sound-absorbing vessel contains an independent chamber;

the interdigital transducer is used to generate a surface acoustic wave based on the basic frequency signal;

the first controller is used to individually control the finger period in each of the interdigital transducers;

the second controller is used to periodically activate part or all of the interdigital transducers;

the first controller and the second controller are further used to construct an array of the interdigital transducers to change the thermal field distribution in the acoustothermal chip.

2. The gene transfection system of claim 1, wherein the thermal field distribution in the acoustothermal chip is changed based on shapes of electrodes of the interdigital transducer.

3. The gene transfection system of claim 1, wherein the second controller is configured to simultaneously activate a group of interdigital transducers in the same one-dimensional direction;

the first controller is configured to control the finger period of the group of interdigital transducers in a one-dimensional direction to change in a gradient; and the first controller and the second controller are configured to construct a two-dimensional interdigital transducer array.

4. The gene transfection system according to claim 1, wherein the interdigital transducer is arranged on the piezoelectric substrate, and the sound-absorbing vessel is provided on the interdigital transducer.

5. The gene transfection system of claim 1, wherein the bottom of the chamber is further coated with polylysine.

6. The gene transfection system of claim 1, wherein the piezoelectric substrate is a 128° Y-cut X-propagation, double-side polished lithium niobate substrate.

* * * * *